(12) United States Patent
Khavinson et al.

(10) Patent No.: US 7,851,449 B2
(45) Date of Patent: Dec. 14, 2010

(54) PEPTIDE, PHARMACEUTICAL COMPOSITION, AND A METHOD OF TREATING MICROCIRCULATION DISORDERS

(75) Inventors: Vladimir Khatskelevich Khavinson, St. Petersburg (RU); Evgeny Iosifovich Grigoriev, St. Petersburg (RU); Vladimir Victorovich Malinin, St. Petersburg (RU); Galina Anatolievna Ryzhak, St. Petersburg (RU)

(73) Assignee: Obschestvo S Ogranichennoi Otvetstvennostyu "SIA Peptides", St. Petersburg (RU)

( * ) Notice: Subject to any disclaimer, the term of this patent is extended or adjusted under 35 U.S.C. 154(b) by 281 days.

(21) Appl. No.: 12/298,411

(22) PCT Filed: Dec. 4, 2006

(86) PCT No.: PCT/RU2006/000652

§ 371 (c)(1),
(2), (4) Date: Oct. 24, 2008

(87) PCT Pub. No.: WO2007/106254

PCT Pub. Date: Nov. 25, 2007

(65) Prior Publication Data

US 2009/0099098 A1    Apr. 16, 2009

(30) Foreign Application Priority Data

May 23, 2006    (RU) ............................. 2006117584

(51) Int. Cl.
*A61K 38/06* (2006.01)
*C07K 5/09* (2006.01)

(52) U.S. Cl. ..................................... 514/21.9; 530/331
(58) Field of Classification Search ........................ None
See application file for complete search history.

(56) References Cited

U.S. PATENT DOCUMENTS 6,727,227 B1    4/2004    Khavinson et al.

FOREIGN PATENT DOCUMENTS

| WO | WO 01/47950 | A | 7/2001 |
| WO | WO 2005/056580 | A | 6/2005 |
| WO | WO 2006/001728 | A | 1/2006 |
| WO | WO 2007/136295 | A2 | 11/2007 |
| WO | WO 2007/139431 | A1 | 12/2007 |
| WO | WO 2007/139435 | A1 | 12/2007 |

OTHER PUBLICATIONS

Mileusnic, R. et al., "The Peptide Sequence Arg-Glu-Arg, Present in the Amyloid Precursor Protein, Protects Against Memory Loss Caused by Abeta and Acts as a Cognitive Enhancer" European Journal of Neuroscience, Apr. 2004, pp. 1933-1938, vol. 19, No. 7, Oxford University Press, Great Britain.

Khavinson, V Kh. et al., "Mechanisms Underlaying Geroprotective Effects of Peptides" Bulletin of Experimental Biology and Medicine, Jan. 2002, pp. 1-5, vol. 133, No. 1, Consultants Bureau, New York, NY.

Korkushko O. V. et al., "Geroprotective Effect of Epithalamine (Pineal Gland Peptide Preparation) in Elderly Subjects with Accelerated Aging" Bulletin of Experimental Biology and Medicine, Sep. 1, 2006, pp. 356-359, vol. 142, No. 3, Kluwer Academic Publishers, NE.

Wang Chao et al., "The Synthesis and Immunosuppressive Activities of Steroid-urotoxin Linkers" Bioorganic & Medicinal Chemistry, Aug. 15, 2004, pp. 4403-4421, vol. 12, No. 16.

Barabanova, S.V. et al., "[Parallel Analysis of C-Fos Protein and Interleukin-2 Expression in Hypothalmic Cells Under Different Influence]" Feb. 2007, pp. 150-160, vol. 92, No. 2, Rossi §SKII Fiziologicheski § Zhurnal Imeni I.M. Sechenova, Rossi §Skaia Akademiia Nauk.

Sibarov, D.A. et al., "Epitalon Influences Pineal Secretion in Stress-Exposed Rats in the Daytime" Neuroendocrinology Letters, 2002, pp. 452-454, vol. 23, No. 5-6, Sweden.

*Primary Examiner*—David S Romeo
(74) *Attorney, Agent, or Firm*—Leydig, Voit & Mayer, Ltd.

(57) ABSTRACT

The invention is related to the medicinal means of correction of metabolic vascular syndrome and diseases, associated with disordered vascular wall permeability and capillaries fragility, and can be used as a means of enhancing capillaries resistance. There is proposed a peptide lysyl-glutamyl-asparagine acid of the general formula H-Lys-Glu-Asp-OH sequence 1 [SEQ ID NO:1], revealing biological activity and capable of enhancing capillaries resistance. There is also proposed a pharmaceutical composition enhancing capillaries resistance, containing effective amount of peptide lysyl-glutamyl-asparagine acid of the general formula H-Lys-Glu-Asp-OH sequence 1 [SEQ ID NO: 1] as its active base and pharmaceutically acceptable carrier. This pharmaceutical composition is in form for parenteral administration. There is proposed a method for prevention and/or treatment of disorders of microcirculation in organs and tissues, consisting in the administration to a patient of the pharmaceutical composition, containing peptide lysyl-glutamyl-asparagine acid of the general formula H-Lys-Glu-Asp-OH sequence 1 [SEQ ID NO: 1] in the dose of 0.01-100 μg/kg of body weight at least once a day during a period necessary for attaining the therapeutic effect, such administration being performed parenterally.

5 Claims, 1 Drawing Sheet

\* - P<0,05 as compared to the control taken as 100%.

PEPTIDE, PHARMACEUTICAL COMPOSITION, AND A METHOD OF TREATING MICROCIRCULATION DISORDERS

The invention is related to the medicinal means of correction of metabolic vascular syndrome and diseases, associated with disordered vascular wall permeability and capillaries fragility, and can be used as a means of enhancing capillaries resistance.

Disorders of blood microcirculation in different organs and tissues are one of the most important links of pathogenesis of the great number of diseases and pathologic states.

There are known preparations normalising vascular permeability and improving metabolic processes in vascular walls. Among these preparations we should name Prodectin, Dicynone, Doxium, Glyvenol, Aescusan (The Comprehensive Russian Encyclopaedia of Medicinal Means, Moscow, Remedium publishing house, V.2, 2002 (rus.), which are used for enhancing and normalization of capillaries permeability in case of different diseases.

But they are not enough effective, have side effects and restricted application in case of blood coagulation disorders.

This makes it necessary to develop new angioprotective medical preparations.

The claimed peptide has no structural analogues on the level of techniques in the prior art.

The claimed invention has set and resolved the task of obtaining the new peptide, possessing biological activity, which manifests itself in the enhancing capillaries resistance and pharmaceutical composition, containing this peptide.

The technical result of the invention consists in the creation of a new peptide, enhancing capillaries resistance, as well as a pharmaceutical composition containing the new peptide as an active base, being used for enhancing capillaries resistance and vascular walls permeability exerting normalising effect on metabolic processes in vascular walls of the cells.

This invention is related to the peptide lysyl-glutamyl-asparagine acid of the general formula H-Lys-Glu-Asp-OH sequence 1 [SEQ ID NO:1].

Peptide lysyl-glutamyl-asparagine acid of the general formula H-Lys-Glu-Asp-OH sequence 1 [SEQ ID NO:1] reveals biological activity of enhancing capillaries resistance.

The other aspect of the invention is related to the pharmaceutical composition enhancing capillaries resistance, containing effective amount of peptide lysyl-glutamyl-asparagine acid of the general formula H-Lys-Glu-Asp-OH sequence 1 [SEQ ID NO: 1] and pharmaceutically acceptable carrier.

This pharmaceutical composition exists in the form, which is intended for parenteral administration.

The next aspect of this invention is related to the method of prevention and/or treatment of microcirculation disorders in organs and tissues, consisting in administration to the patient the pharmaceutical composition containing the effective amount of peptide lysyl-glutamyl-asparagine acid of the general formula H-Lys-Glu-Asp-OH sequence 1 [SEQ ID NO: 1] as its active base, in the dose of 0.01-100 µg/kg of body weight, at least once a day throughout the period necessary for attaining therapeutic effect.

The pharmaceutical composition is administered parenterally.

The peptide lysyl-glutamyl-asparagine acid of the general formula H-Lys-Glu-Asp-OH sequence 1 [SEQ ID NO:1] is obtained by the classical method of peptide synthesis in solution.

The possibility of objective attaining the technical result while using the claimed invention has been confirmed by reliable data represented in the examples, containing the experimental data obtained in the studies performed in accordance with the methods traditional for this field.

The regulating effect of the peptide H-Lys-Glu-Asp-OH on the vascular wall, that is enhancing capillaries resistance and vascular walls durability, was revealed in its experimental study.

The study of the biological activity of the peptide was performed on vascular walls explants, in experimental parodontitis in rats and patients with vascular lesion of different aetiology.

The notion "pharmaceutical composition" means such different medicinal forms containing the new peptide, which may be used in the medicine as a means enhancing capillaries resistance.

To obtain pharmaceutical compositions covered by this invention, the effective amount of peptide H-Lys-Glu-Asp-OH as the active base (active substance) must be mixed with pharmaceutically acceptable carrier according to the methods of compounding, which are universally accepted in pharmaceutics.

The notion "effective amount" implies the use of such amount of the active base, which, according to its quantitative indices of activity and toxicity, as well as to the knowledge of a competent specialist, must be effective in the given medicinal form.

The carrier can have different forms, depending on the medicinal form of the substance, desirable for the administration to the organism.

For parenteral administration, the carrier is usually introduced into the physiological saline solution or sterile water, though other ingredients improving its stability or preserving sterility may also be added.

The subject matter of the claimed invention is explained by a FIGURE and tables.

Table 1 displays the effect of peptide H-Lys-Glu-Asp-OH on morphological and biochemical indices of guinea pig peripheric blood in the study of toxicity.

Table 2 displays the effect of peptide H-Lys-Glu-Asp-OH on skin capillaries resistance in patients with hypovitaminosis.

Table 3 displays the effect of peptide H-Lys-Glu-Asp-OH on the indices of hemostasis in patients suffering from purpura senilis.

The FIGURE displays the effect of peptide H-Lys-Glu-Asp-OH on the development of vascular walls explants.

The invention is illustrated by an example of synthesis of peptide lysyl-glutamyl-asparagine acid of the general formula H-Lys-Glu-Asp-OH sequence 1 [SEQ ID NO:1] (Example 1), by examples of studies of toxicity and biological activity of the peptide (Examples 2, 3, 4, 5, 6, 7), as well as by the results of the peptide's clinical administration, demonstrating its pharmacological properties and confirming the possibility of attaining preventive and/or therapeutic effect (Examples 5, 6).

EXAMPLE 1

Synthesis of H-Lys-Glu-Asp-OH Peptide

Figure 1:
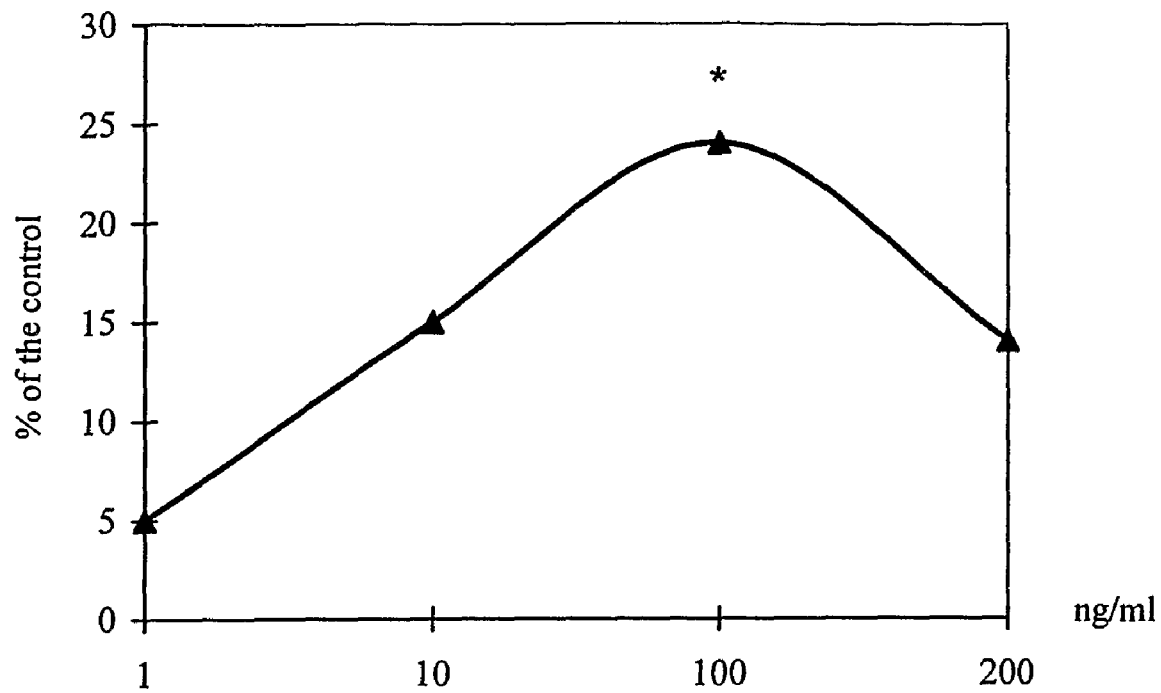
FIG. 1 displays the effect of peptide H-Lys-Glu-Asp-OH on the development of vascular wall.

1. Product name: lysyl-glutamyl-asparagine acid.
2. Structural formula:

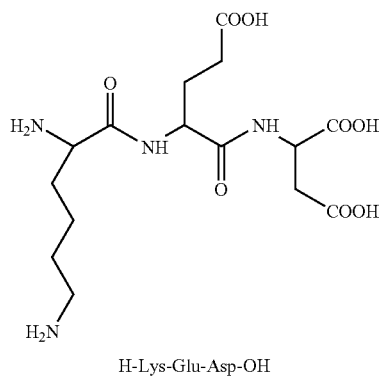

H-Lys-Glu-Asp-OH

3. Molecular formula without ion pair: $C_{15}H_{26}N_4O_8$.
4. Molecular weight without ion pair: 390.39.
5. Ion pair: acetate.
6. Appearance: white amorphous powder without smell.
7. Method of synthesis: the peptide is obtained by a classical method of synthesis in a solution by the following scheme:

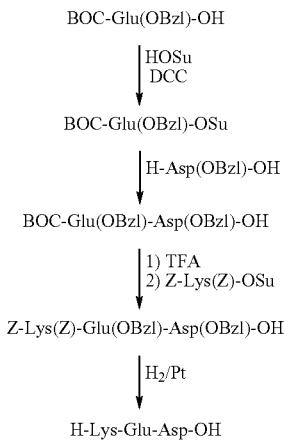

BOC—tert·butyloxycarbonyl group,
Z—benzyloxycarbonyl group,
OSu—N-oxysuccinimide ester,
DCC—N,N'-dicyclohexylcarbodiimide,
OBzl—benzyl ester,
TFA—trifluoracetic acid.

Properties of the Finished Product:
  peptide content 98.15% (by HPLC, 220 nm);
  thin layer chromatography (TLC)— individual, $R_f=0.65$ (acetonitrile-water 1:3);
  moisture content: 6%;
  pH of 0.01%-solution: 4.77;
  specific rotary power: $[\alpha]_D^{22}$: $-31°$ (c=1, $H_2O$), "Polamat A", Carl Zeiβ Jena.

Example of Synthesis

1) BOC-Glu(OBzl)-OSu, N-oxysuccinimide ester N-tert.butyloxycarbonyl-(γ-benzyl)glutamin acid (I)

33.7 g (0.1 mole) of N-tert.butyloxycarbonyl-(γ-benzyl) glutamin acid BOC-Glu(OBzl)-OH is dissolved in 50 ml of N,N'-dimethylformamide and cooled down to $-10°$ C., added cooled (4-6° C.) solutions of N,N'-dicyclohexylcarbodiimide (23.0 g, 0.11 mole) in 30 ml of N,N'-dimethylformamide and N-hydroxysuccinimide (13.0 g, 0.11 mole) in 20 ml of N,N'-dimethylformamide. The mixture is stirred for 12 hours, being cooled by ice, and then for 24 hours at room temperature. The precipitated N,N'-dicyclohexylcarbamide is filtered and the received solution of activated ether is used without isolation in the next stage.

2) BOC-Glu(OBzl)-Asp(OBzl)-OH, N-tert.butyloxycarbonyl-(γ-benzyl)glutamyl-(β-benzyl)aspartate (II)

28.0 g (0.12 mole) of (β-benzyl)asparagine acid H-Asp(OBzl)-OH and 36 ml (0.12 mole) of triethylamine are suspended in 50 ml of N,N'-dimethylformamide and stirred for 1 hour. Then in portions there is added a solution of activated ether BOC-Glu(OBzl)-OSu (I), obtained in the previous stage. The mixture is stirred at room temperature for 48 hours. Then it is acidified by 0.5 n of sulphuric acid up to pH 2-3 and extracted by ethyl acetate (4×50 ml). The product is washed in 0.5N sulphuric acid solution (3×50 ml), water (2×50 ml), 5% $NaHCO_3$ (2×50 ml), water (2×50 ml), saturated NaCl solution 2×50 ml. The organic layer is dried over $Na_2SO_4$. The solvent is removed in vacuo and the residue is crystallised in the hexane system. 50 g of the product is obtained (92%). $R_f=0,34$ (benzene-acetone 2:1).

3) TFA H-Glu(OBzl)-Asp(OBzl)-OH (III), (γ-benzyl)glutamyl-(β-benzyl) aspartate trifluoracetate 5.68 g ($\approx$0.01 mole) of N-tert.butyloxycarbonyl-(γ-benzyl) glutamyl-(β-benzyl)aspartate (I) is dissolved in 20 ml of dichlormethan-trifluoracetic acid mixture (3:1). Two hours later the solvent is removed in vacuo at 40° C. The removal is repeated with an addition of another portion of dichlormethan (2×10 ml). The residue is dried in vacuo over NaOH. 5.80 g ($\approx$100%) of oil is obtained. $R_f=0.63$ (n-butanol-pyridine-acetic acid-water, 15:10:3:12).

4) Z-Lys(Z)-Glu(OBzl)-Asp(OBzl)-OH (IV), N,$N^\epsilon$-dibenzyloxycarbonyllysyl-(γ-benzyl)glutamyl-(β-benzyl)aspartate 5.65 g (0.01 mole) of (γ-benzyl)glutamyl-(β-benzyl)aspartate trifluoracetate (III) is dissolved in 10 ml of dimethylformamide, added 2.80 ml (0.02 mole) of triethylamine and 6.64 g (0.013 mole) of N-oxysuccinimide ester of N,$N^\epsilon$-dibenzyloxycarbonyllysine. The mixture is stirred for 24 hours at room temperature.

The product is precipitated with 0.5N sulphuric acid solution (150 ml), extracted by ethyl acetate (3×30 ml), washed in 0.5N sulphuric acid solution (2×20 ml), water, 5% sodium bicarbonate solution (1×20 ml), water, 0.5N sulphuric acid solution (2×20 ml), water and dried over anhydrous sodium sulphate. Ethyl acetate is filtered and removed in vacuo at 40° C. The residue is crystallised in the ethyl acetate/hexane system. The product is filtered and dried in vacuo over $P_2O_5$. The yield is 6.04 g (72%). The temperature of melting ($T_{m1}$) is 142° C. $R_f=0.60$ (benzene-acetone, 1:1).

5) H-Lys-Glu-Asp-OH (V), lysyl-glutamyl-aspartate

Protected tripeptide Z-Lys(Z)-Glu(OBzl)-Asp(OBzl)-OH (IV) (0.90 g) is dissolved in the mixture of methyl spirit-water (4:1) and hydrated over catalyst Pd/C (5%) for 4 hours. The fullness of deblockading reaction is controlled by TLC in acetonitrile-water system (1:3). Solvent is removed in vacuo, residue is dried in vacuo over KOH For the purpose of purification 300 mg of preparation is dissolved in 4 ml of 0.01% trifluoracetic acid and subjected to highly productive liquid chromatography on reverse phase column 50×250 mm Diasorb-130-C16T, 7 μm. Chromatographer Beckman System Gold, 126 Solvent Module, 168 Diode Array Detector Module. Conditions of chromatography: A: 0,1% TFA; B: MeCN/0,1% TFA, gradient B 0→50% in 100 minutes. Sample volume 5 ml, detection at 215 nm, scanning 190-600 nm, flow rate 10 ml/min. Fraction is selected for 42,0-47,0 minutes. The solvent is removed in vacuo at the temperature not higher than 40° C., the removal is several times (5 times) repeated with 10 ml of 10% acetic acid solution. Finally the residue is dissolved in 20 ml of deionized water and lyophilized.

270 mg of purified substance in the form of amorphous white powder without smell is obtained.

6) Analysis of the Ready Substance

Peptide content is defined by HPLC on Phenomenex C18 LUNA column, 4,6×150 mm. A: 0.1% of TFA; B: MeCN; grad.B 0-100% in 10 min. The flow rate is 1 ml/min. Detection by 220 nm, scanning—by 190-600 nm, the sample volume is 20 μl. Base substance content—98.15%.

TLC: individual, $R_f$=0.65 (acetonitrile/water, 1:3). Sorbfil plates, 8-12 μm Silicagel, developing in chlorine/benzidine.

Moisture content: 6% (gravimetrically, according to the mass loss by drying, −20 mg at 100° C.).

pH of 0.01% solution: 4.77 (potentiometrically)

Specific rotary power: $[\alpha]_D^{22}$: −31° (c=1, $H_2O$), "Polamat A", Carl Zeiβ Jena.

EXAMPLE 2

Study of Peptide H-Lys-Glu-Asp-OH Toxicity

Common toxicity of peptide H-Lys-Glu-Asp-OH was studied according to the requirements stated in the "Manual for experimental (pre-clinical) study of new pharmacological substances" (2000): acute toxicity in case of single administration of the substance and sub-acute and chronic toxicity in case of long-term administration of the peptide.

The study of acute toxicity was performed on 66 white mongrel male mice with body weight of 20-23 g. The animals were randomly subdivided into 6 equal groups. The substance was administered to the animals once, intramuscularly, in the doses of 1 mg/kg, 2 mg/kg, 3 mg/kg, 4 mg/kg, 5 mg/kg in 0.25 ml of sterile 0.9% NaCl solution. The control animals received 0,9% NaCl solution in the same volume.

The study of sub-acute toxicity was performed on 60 white mongrel male rats with body weight of 160-240 g. Experimental animals received the substance daily, intramuscularly for 90 days in the doses of 1 μg/kg, 0.1 mg/kg, 1 mg/kg in 0.5 ml of sterile 0.9% NaCl solution. Control animals received sterile 0.9% NaCl solution in the same volume. Morphology and properties of the animals' peripheral blood were studied before the administration of the substance, as well as on the $30^{th}$, $60^{th}$ and $90^{th}$ day after the beginning of the administration. Upon completion of the experiment biochemical and coagulologic indices of the blood were also evaluated.

The studies of chronic toxicity were conducted for 6 months, basing on the term of recommended clinical administration of the substance, on 96 male guinea pigs with body weight of 300-340 g. Experimental animals received the peptide daily, once a day, intramuscularly, for 6 months in the doses of 1 μg/kg, 0.1 mg/kg, 1 mg/kg in 0.5 ml of sterile 0.9% NaCl solution. Control animals received sterile 0.9% NaCl solution in the same volume and by the same schedule. Traditional methods were used for the evaluation of the following indices of the animals' peripheral blood: the quantity of erythrocytes, hemoglobin, reticulocytes, thrombocytes, leukocytes, leukocyte formula, erythrocyte sedimentation rate (ESR), erythrocyte resistance. Alongside with that, the content of total protein in the serum was identified using Lowry's method, as well as potassium and sodium content using the method of plasma spectrophotometry. Upon the completion of the experiment pathomorphologic studies of animal brain and spinal cord, spinal cord ganglia, thyroid gland, parathyroid glands, adrenal glands, testis, pituitary body, heart, lungs, aorta, liver, kidneys, urinary bladder, pancreas, stomach, small intestine, large intestine, thymus, spleen, lymph nodes and bone marrow were performed.

The study of acute toxicity showed, that a single administration of the studied peptide to animals in the dose exceeding the therapeutic one, which is recommended for clinical administration, by more than 5000 times, does not cause toxic reactions, which points out the width of diapason of possible therapeutic doses of the substance.

The study of subacute and chronic toxicity of the peptide showed the absence of any side effects in case of long-term administration of the substance in doses exceeding the therapeutic one by 100-1000 times. The study of peptide effect on guinea pig blood morphology and biochemical indices in 3 and 6 months after the beginning of the substance administration showed that no statistically significant changes in the studied indices took place (Table 1).

Other indices of the morphological blood content of the animals practically didn't change. There weren't registered any reliable effect of the substance on ESR, erythrocyte resistance and blood serum biochemical indices. The evaluation of the animals' general status, of morphologic and biochemical indices of peripheral blood, of morphological status of the organs, of the status of cardiovascular and respiratory systems, as well as of liver and kidney functions revealed no pathologic alterations in the organism.

The absence of common toxicity allows to recommend the pharmaceutical composition, containing the peptide H-Lys-Glu-Asp-OH as its active base, for clinical studies.

EXAMPLE 3

Effect of H-Lys-Glu-Asp-OH Peptide on Development of Vascular Wall Explants

The experiments were conducted on 32 fragments of vascular wall from the peripheral artery of Wistar rats with body weight of 150-200 g. Nutritional medium for explants cultivation consisted of 35% Eagle's solution, 25% calf fetal serum, 35% Hanx solution, 5% chicken embryonic extract, with the addition of glucose (0.6%), insulin (0,5 units/ml), penicillin (100 units/ml), glutamine (2 mM). Vascular wall fragments were placed into this medium and cultivated in Petri dishes in the thermostat at the temperature of 36.7° C. for 48 hours. Peptide H-Lys-Glu-Asp-OH was added into the medium, in the concentration of 1, 10, 100 and 200 ng/ml.

Area index (AI), i.e. the ratio of total explant area together with the growth zone to the initial area of vascular wall fragment served as the criterion of biologic activity. AI values were expressed in percent, control AI values being considered as 100%.

The FIGURE displays the effect of peptide H-Lys-Glu-Asp-OH on the development of vascular wall.

It was found, that after 24 hours of cultivating the explants sprawled upon the collagen substrate, and proliferating and migrating cells began disseminating around the area of the explant. By the 3$^{rd}$ day of the cultivation in case of peptide H-Lys-Glu-Asp-OH making 100 ng/ml a statistically significant AI growth by 24% was observed as compared to the control AI indices. The study of vascular wall explants after longer periods (7 days) of cultivating revealed the same stimulating effect of H-Lys-Glu-Asp-OH peptide in case of the same concentrations.

Thus H-Lys-Glu-Asp-OH peptide exerted tissue specific effect on vascular wall tissue stimulating explants growth.

EXAMPLE 4

Effect of H-Lys-Glu-Asp-OH Peptide on Microcirculation in Rats with Experimental Parodontitis The experiments were conducted on 45 white mongrel male and female rats with body weight of 180-200 g. The model of light parodontitis was induced by the method of differentiated feeding of rats with standard granulated PK-120 forage for 1.5 months.

The animals were divided into 3 groups 15 rats in each: the animals of the first group, suffering from parodontitis didn't receive any treatment, rats in the second group suffering from experimental parodontitis were injected with 0.1 ml of sterile 0.9% NaCl solution into the mucous of the gingiva transitional fold (control); the animals of the third group with experimental parodontitis were subjected to a daily single injection of H-Lys-Glu-Asp-OH peptide in the dose of 2 µg in the 0.1 ml of sterile 0,9% NaCl solution into the mucous gingiva transitional fold with simultaneous rubbing in of peptide solution for 10 days.

During all experiments there was conducted a biomicroscopy of mucous membrane of the rats gingiva under nembutal anaesthesia with usage of contact object lenses and estimated the blood flow rate in capillaries by means of laser capillary blood flow analyzer LAKK-01. The studies were conducted in 3 areas of the gingiva, in the free gingiva, attached gingiva and transitional fold in case of 100 magnification. Clinical signs of the parodontitis were evaluated visually.

Biomicroscopic estimation of the microcirculatory bed in tissues of the parodentium in animals of the first group showed the predominance of the inflammatory changes in microvessels, which is especially seen in the free gingiva. In this part the capillaries are dilated and the blood flow is evidently slowed. In venule part the capillaries are overloaded with blood due to disorder of venous outflow. Perivascular tissue is edematous, background is blurred. Capillaries forward, there were registered diffuse perivascular hemorrhages, evidencing significant increase in the level of walls permeability.

Mentioned signs of the microcirculation disorders also remain in the part of the attached gingiva, though they are less pronounced. In the transitional gingival fold signs of microcirculation disorders are more diverse: in the surface layer of the mouth cavity mucous membrane there are hyperemic capillaries with leucocytes adhesion and diapedesis hemorrhages, especially pronounced in postcapillary part of the microcirculatory bed. In deep layers of the mucous membrane against the background of tissues edema there appear hyperemic arterioles with strained contours as well as hyperemic venules with slowed grainy blood flow. The highest index of microcirculation (IM), describing total point evaluation of microcirculation disorder, was registered in case of gingivitis in the free gingiva and made 0.54±0.01, that is 2-fold higher than in normal parodontium (0.21±0.30). This index in the attached gingiva was 0.31±0.08, and in the area of transitional fold—0.27±0.04. The morphometric study showed that there was an increase in the diameter of the capillaries in all parts of the gingiva: 9.7±0.21 µm in the free gingiva, 8.9±0.25 µm in the attached gingiva and 8,7±0.11 µm in the transitional fold. In all studied parts there was registered an increase in the level of capillaries density per area unit compared to the healthy parodontium tissues in the average up to 40±1.2 mm$^2$ (norm—29.3±2.3 mm$^2$). Laser dopplerography showed an increase in the blood flow rate in all parts of gingiva: 29±1.2 conv. units in the free gingiva, 27±0.5 conv. units in the attached gingiva; 22±1.0 conv. units in the transitional fold (norm—18±1.3 conv. units). Examination of the gingival mucous membrane in rats of the second group (control) revealed an extended change of its color from pale pink to brightly red with blue tint. Biomicroscopy of the mucous membrane revealed further worsening of parodontium tissue trophic supply in the form of progressing disorder of microcirculation. Thus, blood flow in the capillaries and minor venules of free and attached gingivae was grainy and slowed with local erythrocytes aggregation. Vascular contours became twisted and strained. The permeability of the hystohematic barrier was significantly increasing, this was evidenced by the edema of interstice in the form of background dimness and diffuse perivascular hemorrhages. There were registered signs of the intensive proliferative endothelium activity, which consisted in the increased microvessels crimpiness and capillary loop duplication phenomenon, as a compensatory reaction on microcirculation disorder and developing tissue hypoxia. These changes were most pronouncedly seen in the attached gingiva and in surface layers of the transitional fold. In the transitional fold together with prominent decrease in the blood flow rate there were registered reduction in the number of functioning capillaries and changes of the capillary loops shape as they became more twisted and there emerged varicosis. Capillary background was blurred, capillaries contours were not even, this reflected disorders in the barrier resources of capillary walls with progressing of perivascular hemorrhages. It should be emphasized that microcirculatory bed structural deformation signs were preceded by the generalization of the pathologic process in gingival tissues, which should be regarded as a sign of unfavorable prognosis. These group of experiments revealed further increase in the level of microcirculation disorders in parodontium tissues and increase of IM in the free gingiva up to 0.75±0.03; in the attached gingiva up to 0.63±0.04; in the transitional fold up to 0.39±0.02.

Morphometry of the microvessels diameters in the studied parts of the gingiva mucous membrane in these experiments showed their further widening (12.3±0.36 in the free gingiva, 9.8±0.35 in the attached gingiva, 9.1±0.09 in the transitional fold) together with the definite decrease in the capillary density per area unit in the average to 30±1.5 mm$^2$. Laser dopplerography revealed a pronounced decrease in blood flow rate in all parts of gingiva: 15±1.5 conv. units in the free gingiva, 17±0.7 conv. units in the attached gingiva; 19±1.2 conv. units in the transitional fold.

Examination of the gingival mucous membrane in rats subjected to peptide H-Lys-Glu-Asp-OH injections, revealed changes of its color (it became pale pink) and decrease in hydropic and inflammatory reaction, especially in the area of the transitional fold and attached gingiva. Biomicroscopy of the mucous membrane in general revealed a pronounced correction of pathologic re-construction of the microcirculatory bed and subsidence of the tissues inflammation and edema.

Changes of the microcirculation mostly remained in the free gingiva. Capillaries in this part were a bit dilated, but the blood flow rate in them had abruptly increased and blood flow became homogenous. Capillaries contours were more or less even, without any signs of erythrocytes diapedes, their capillaroscopic surrounding was transparent, which evidenced restoration of the disordered hystohematic barrier permeability. In the attached gingiva and transitional fold the biomicroscopy of gingival mucous membrane revealed complete correction of the microcirculation: significantly increased the number of functioning capillaries, their contours became even and distinct, blood flow remained a bit grainy, there were no signs of permeability disorders and tissues perivascular edema.

In the transitional fold and deep layers of the mucous membrane in some venules there remained grainy blood flow. IM in the free gingiva decreased to the level of normal parodotium—0.29±0.15; and in the attached gingiva and transitional fold—0.22±0.05 and 0.20±0.18 correspondingly. Morphometry revealed decrease in the diameter of the capillaries in all parts of the gingival (8.2±0.1 in the free gingiva, 7.8±0.20 in the attached gingiva and 6.57±0.1 in the transitional fold) against the background of their high density per area unit, which was 34±2.7 $mm^2$ in the average. Laser dopplerography indices reduced almost to normal values (20±0.9 conv. units in the free gingiva, 20±1.1 conv. units in the attached gingiva; 19±2.3 conv. units in the transitional fold.

Thus experimental studies showed that H-Lys-Glu-Asp-OH peptide exerts normalizing effect on capillary walls status, increasing their resistance and permeability, as well as on the microcirculatory bed of the gingival and parodontium mucous membrane.

EXAMPLE 5

Effect of H-Lys-Glu-Asp-OH Peptide on Skin Capillary Resistance in Patients with Hypovitaminosis The study was conducted on 25 patients aged 19-35, reporting signs of hypovitaminosis in spring. The patients were randomly divided into 2 groups.

The patients of the main group were divided into three sub-groups depending on the hypovitaminosis severity. Patients suffering from the severe hypovitaminosis were subjected to a daily single intramuscular injection of pharmaceutical composition containing H-Lys-Glu-Asp-OH peptide as its active base, in the dose of 5.0 mg in 1.0 ml of sterile 0.9% NaCl solution for 10 days; patients with moderately sever hypovitaminosis—in the dose of 100.0 μg, and patients with mild signs of hypovitaminosis—in the dose of 1.0 μg.

Control group consisted of 18 patients, subjected to an injection of physiological solution following the same scheme. Both groups received only balanced vitamin containing diet.

The estimation of the H-Lys-Glu-Asp-OH peptide effect on resistance of skin capillaries was conducted by means of Rumpel-Leede-Konchalovskiy capillary fragility test. A blood-pressure cuff was applied to the upper part of the arm of the patients. Then there was maintained pressure up to 200 mmHg for 3 minutes. Skin capillary resistance was evaluated on the area of the dosed load on skin capillaries (under the cuff). Hemorrhages were counted with a help of the magnifying glass.

Skin capillary resistance was graded according to the five-point scale:

I—up to 5 small petechiae,
II—from 6 to 15,
III—up to 30,
IV—more than 30 hemorrhages,
V—innumerable hemorrhages, confluent reaction.

The results of the conducted study showed that application of peptide H-Lys-Glu-Asp-OH contributes to the enhancing skin capillary resistance, which consists in the reliable decrease in the number of skin hemorrhages from 30-47, reported by the patients of the both groups before treatment, to 6-8 in patients of the main group after the treatment, while the number of hemorrhages in patients of the control group remained unchanged (Table 2).

Thus the application of the pharmaceutical composition, containing H-Lys-Glu-Asp-OH peptide as its active base in different doses is expedient in complex therapeutic treatment of patients suffering from hypovitaminosis aiming at increasing capillary resistance and vascular fragility prevention.

EXAMPLE 6

Efficacy of H-Lys-Glu-Asp-OH Peptide Application in Patients with Purpura Senilis The study was conducted on 23 patients aged 70-82, suffering from purpura senilis, who complained of frequent spontaneous hemorrhages on the face, neck, forearms and hands. The patients reported progressive development of the disease.

In the past all the patients underwent symptomatic and pathogenic therapy courses aiming at particular clinical symptoms of vascular pathology.

The patients were randomly divided into two groups. The main group consisted of 12 patients, who were injected with pharmaceutical composition, containing peptide H-Lys-Glu-Asp-OH as its active base, in the dose of 100 μg in 1.0 ml of physiological solution daily intramuscularly for 10 days. Control group consisted of 11 patients, injected with sterile physiological solution following the same scheme.

Complains of the patients were analyzed in dynamics, also there were conducted general blood and urine tests, blood biochemical test. In order to study hemostasis there were made blood coagulogramm and Hess test with a tourniquet.

Unlike control group, the patients of the main group after the administration of the pharmaceutical composition containing peptide H-Lys-Glu-Asp-OH as its active base in different doses, showed more pronounced normalizing effect of peptide on the studied hemostasis indices, which practically reached the level of those in healthy patients (time of recalcification, prothrombin time, activated partial thromboplatinum time, ethanol test); control patients reported only slight unreliable improvement of hemostasis indices (Table 3).

The results of the study showed that after the administration of pharmaceutical composition containing H-Lys-Glu-Asp-OH peptide as its active base in different doses, patients with purpura senilis reported improvement of the skin state and increase in vascular walls durability, evidenced by the results of Hess test, showing the reduction in the number of hemorrhages.

Thus, the administration of the pharmaceutical composition containing peptide H-Lys-Glu-Asp-OH as its active base, is expedient for the treatment of patients with purpura senilis for increasing the level of capillary walls resistance and durability as well as normalization of blood microcirculation.

TABLE 1

| | Administration of peptide H-Lys-Glu-Asp-OH (1 μg/kg) | | | |
|---|---|---|---|---|
| | 3 months | | 6 months | |
| Index | Control (n = 24) | Peptide (n = 24) | Control (n = 24) | Peptide (n = 24) |
| Erythrocytes, $\times 10^{12}/l$ | 5.3 ± 0.6 | 5.4 ± 0.2 | 5.4 ± 0.3 | 5.2 ± 0.4 |
| Hemoglobin, g/l | 14.2 ± 1.4 | 13.8 ± 1.2 | 14.5 ± 1.3 | 14.2 ± 0.6 |
| Reticulocytes, % | 1.3 ± 0.07 | 1.2 ± 0.07 | 1.1 ± 0.05 | 1.3 ± 0.08 |
| Thrombocytes, $\times 10^9/l$ | 143.7 ± 7.9 | 143.6 ± 8.4 | 144.5 ± 8.6 | 144.9 ± 9.8 |
| Leukocytes, $\times 10^9/l$ | 9.4 ± 0.5 | 11.2 ± 0.8* | 9.6 ± 0.5 | 11.9 ± 0.5* |
| Stab neutrophils, % | 0.31 ± 0.04 | 0.27 ± 0.07 | 0.33 ± 0.04 | 0.36 ± 0.05 |
| Segmented neutrophils, % | 45.8 ± 2.1 | 44.9 ± 2.5 | 46.2 ± 3.5 | 43.4 ± 3.2 |
| Eosinophils, % | 0.69 ± 0.05 | 0.64 ± 0.04 | 0.72 ± 0.04 | 0.75 ± 0.08 |
| Basophils, % | 0.61 ± 0.04 | 0.69 ± 0.05 | 0.72 ± 0.03 | 0.71 ± 0.05 |
| Monocytes, % | 2.5 ± 0.02 | 2.4 ± 0.03 | 2.6 ± 0.06 | 2.5 ± 0.05 |
| Lymphocytes, % | 48.9 ± 2.5 | 50.7 ± 2.4 | 51.3 ± 2.7 | 52.7 ± 2.2 |
| ESR, mm/hour | 1.69 ± 0.05 | 1.87 ± 0.07 | 2.01 ± 0.05 | 2.05 ± 0.04 |
| Erythrocytes resistance, % NaCl | | | | |
| maximum | 0.41 ± 0.02 | 0.43 ± 0.04 | 0.42 ± 0.04 | 0.44 ± 0.04 |
| minimum | 0.32 ± 0.05 | 0.33 ± 0.02 | 0.34 ± 0.04 | 0.35 ± 0.05 |
| Total protein in the blood serum, g/l | 72.9 ± 3.1 | 72.6 ± 3.3 | 73.1 ± 3.4 | 73.1 ± 3.6 |
| Sodium in the blood serum, mmole/l | 153.9 ± 5.7 | 154.8 ± 6.8 | 155.5 ± 6.2 | 154.6 ± 6.9 |
| Potassium in the blod serum, mmole/l | 5.1 ± 2.3 | 5.3 ± 1.8 | 5.2 ± 2.1 | 5.4 ± 2.2 |

*P < 0.05 compared to the control

TABLE 2

| | Cuff test indices, points | |
|---|---|---|
| Group of patients | Before administration | After administration |
| Control | III-IV | III-IV |
| H-Lys-Glu-Asp-OH peptide | III-IV | II* |

*P < 0.05 as compared to the indices in patients before administration

TABLE 3

| | | Patients suffering from purpura senilis | |
|---|---|---|---|
| Index | Healthy people | Control | H-Lys-Glu-Asp-OH peptide |
| Time of recalcification | 178.0 ± 14.0 | 147.3 ± 4.2* | 164.2 ± 2.4** |
| Prothrombin time, sec | 12.5 ± 0.1 | 12.4 ± 0.4 | 13.3 ± 0.1* |
| Activated partial thromboplastin time, sec | 32.3 ± 2.1 | 48.0 ± 1.3* | 58.9 ± 0.7** |
| Thrombin time, c | 18.2 ± 0.6 | 16.0 ± 0.2* | 17.1 ± 0.2 |
| Fibrinogen, g/l | 3.2 ± 0.4 | 2.9 ± 0.1 | 2.5 ± 0.1 |
| Ethanol test, % of the positive cases | 0 | 43.8* | 14.3** |
| Euglobulin fibrinolysis, min | 150.0 ± 6.8 | 163.5 ± 5.0 | 156.2 ± 3.9 |

*P < 0.05 compared to the index of healthy people;
**P < 0.05 compared to the control index.

The invention claimed is:

1. An isolated peptide of the formula H-Lys-Glu-Asp-OH.

2. A pharmaceutical composition comprising the peptide of claim 1 and a pharmaceutically acceptable carrier.

3. The pharmaceutical composition according to claim 2, which is a parenteral formulation.

4. A method of treating microcirculation disorders in organs and tissues, which consists of administering to the patient a composition containing peptide of the formula H-Lys-Glu-Asp-OH as its active base in the dose of 0.01-100 µg/kg of body weight at least once a day during a period necessary for attaining the therapeutic effect.

5. The method according to claim 4 wherein the composition is administered parenterally.

* * * * *

SEQUENCE LISTING

```
<160> NUMBER OF SEQ ID NOS: 1

<210> SEQ ID NO 1
<211> LENGTH: 3
<212> TYPE: PRT
<213> ORGANISM: Artificial
<220> FEATURE:
<223> OTHER INFORMATION: Peptide compound H-Lys-Glu-Asp-OH enhancing
      capillaries resistance by means of a normalizing effect on
      metabolic processes in vascular wall cells.
```

```
-continued

<400> SEQUENCE: 1

Lys Glu Asp
1
```